US008784383B2

(12) United States Patent
Cole et al.

(10) Patent No.: US 8,784,383 B2
(45) Date of Patent: Jul. 22, 2014

(54) INSULIN PUMP DERMAL INFUSION SET HAVING PARTIALLY INTEGRATED MECHANIZED CANNULA INSERTION WITH DISPOSABLE ACTIVATION PORTION

(75) Inventors: Russell S. Cole, New York, NY (US); Christopher J. Kadamus, Jamaica Plain, MA (US); Stephen J. Irwin, Arlington, MA (US); Serge Roux, Boston, MA (US); Eric Bené, Lynn, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 48 days.

(21) Appl. No.: 13/302,915

(22) Filed: Nov. 22, 2011

(65) Prior Publication Data

US 2012/0143135 A1 Jun. 7, 2012

Related U.S. Application Data

(60) Provisional application No. 61/344,966, filed on Nov. 30, 2010, provisional application No. 61/457,033, filed on Dec. 13, 2010.

(51) Int. Cl.
*A61M 5/178* (2006.01)

(52) U.S. Cl.
USPC ............ 604/164.01; 604/164.04; 604/164.12; 604/180

(58) Field of Classification Search
USPC ............ 604/117, 136–137, 156–157, 164.01, 604/164.04, 164.11, 164.12, 174, 180
See application file for complete search history.

(56) References Cited

U.S. PATENT DOCUMENTS 3,918,355 A 11/1975 Weber
4,490,141 A 12/1984 Lacko et al.
6,093,172 A * 7/2000 Funderburk et al. .......... 604/135
7,648,494 B2 * 1/2010 Kornerup et al. ............ 604/539
7,713,258 B2 5/2010 Adams et al.
8,172,803 B2 5/2012 Morrissey et al.
8,221,359 B2 7/2012 Kristensen et al.
8,262,618 B2 9/2012 Scheurer
8,277,415 B2 10/2012 Mounce et al.
8,285,328 B2 10/2012 Caffey et al.
8,287,467 B2 10/2012 List et al.

(Continued)

FOREIGN PATENT DOCUMENTS

WO WO 2009/010399 A1 1/2009
WO WO 2009/039013 A1 3/2009
WO WO 2010/112521 A1 10/2010

*Primary Examiner* — Theodore Stigell
(74) *Attorney, Agent, or Firm* — Roylance, Abrams, Berdo and Goodman, LLP

(57) ABSTRACT

An infusion set has a partially integrated ballistic inserter that can insert a needle at a controlled rate of speed to a depth to deliver content to the upper 3 mm of skin surface, and a skin-securing adhesive layer to secure the skin surface at the insertion site such that the inserter that can insert a needle with a reduced risk of tenting of the skin surface. A removable turnkey or pushable handle can be provided to release a driving spring of the ballistic inserter to insert a needle at a controlled rate of speed, of 3.3 ft/sec. (1.0 m/sec.) up to and including those greater than 10 ft/sec. (3.0 m/sec.), then release from the set for disposal. The infusion set can further include an extendable interface ring that retracts when the inserter is removed from the infusion set.

17 Claims, 12 Drawing Sheets

16
18
12
19
20
21
21
30
22
24
10
26
28
27
33
32
31
34
14
36

(56) References Cited

U.S. PATENT DOCUMENTS

| | | | |
|---|---|---|---|
| 8,287,516 | B2 | 10/2012 | Kornerup et al. |
| 8,306,596 | B2 | 11/2012 | Schurman et al. |
| 8,310,415 | B2 | 11/2012 | McLaughlin et al. |
| 8,313,468 | B2 | 11/2012 | Geipel et al. |
| 2004/0044306 | A1 | 3/2004 | Lynch et al. |
| 2005/0101912 | A1 | 5/2005 | Faust et al. |
| 2006/0001551 | A1 | 1/2006 | Kraft et al. |
| 2006/0173410 | A1 | 8/2006 | Moberg et al. |
| 2007/0093754 | A1 | 4/2007 | Mogensen et al. |
| 2007/0219496 | A1 | 9/2007 | Kamen et al. |
| 2008/0103483 | A1 | 5/2008 | Johnson et al. |
| 2008/0319414 | A1 | 12/2008 | Yodfat et al. |
| 2009/0012472 | A1 | 1/2009 | Ahm et al. |
| 2009/0198191 | A1 | 8/2009 | Chong et al. |
| 2009/0198215 | A1 | 8/2009 | Chong et al. |
| 2009/0240240 | A1 | 9/2009 | Hines et al. |
| 2009/0254041 | A1 | 10/2009 | Krag et al. |
| 2009/0326457 | A1 | 12/2009 | O'Connor |
| 2010/0049129 | A1 | 2/2010 | Yokoi et al. |
| 2010/0160902 | A1 | 6/2010 | Aeschilimann et al. |
| 2010/0286714 | A1 | 11/2010 | Gyrn et al. |
| 2010/0291588 | A1 | 11/2010 | McDevitt et al. |
| 2010/0298830 | A1 | 11/2010 | Browne et al. |
| 2012/0253282 | A1 | 10/2012 | Nagel et al. |
| 2012/0259185 | A1 | 10/2012 | Yodfat et al. |
| 2012/0265034 | A1 | 10/2012 | Wisniewski et al. |
| 2012/0277554 | A1 | 11/2012 | Schurman et al. |
| 2012/0277667 | A1 | 11/2012 | Yodat et al. |
| 2012/0277724 | A1 | 11/2012 | Larsen et al. |
| 2012/0283540 | A1 | 11/2012 | Brüggemann |
| 2012/0291778 | A1 | 11/2012 | Nagel et al. |
| 2012/0293328 | A1 | 11/2012 | Blomquist |
| 2012/0296269 | A1 | 11/2012 | Blomquist |
| 2012/0296310 | A1 | 11/2012 | Blomquist |
| 2012/0296311 | A1 | 11/2012 | Brauker et al. |

* cited by examiner 118
121
126
121
131
116
127

INSULIN PUMP DERMAL INFUSION SET HAVING PARTIALLY INTEGRATED MECHANIZED CANNULA INSERTION WITH DISPOSABLE ACTIVATION PORTION

CROSS-REFERENCE TO RELATED APPLICATIONS

This application claims the benefit under 35 U.S.C. §119 (e) of a U.S. provisional patent application of Russell Cole et al. entitled "Insulin Pump Dermal Infusion Set Having Partially Integrated Mechanized Cannula Insertion With Disposable Activation Key", Ser. No. 61/344,966, filed on Nov. 30, 2010, and a U.S. provisional patent application of Russell Cole et al. entitled "Insulin Pump Dermal Infusion Set Having Partially Integrated Mechanized Cannula Insertion With Disposable Activation Key", Ser. No. 61/457,033, filed on Dec. 13, 2010, the entire content of both said applications being incorporated herein by reference.

FIELD OF THE INVENTION

The present invention relates generally to insulin infusion sets, including a partially integrated inserter for an infusion set, which ensures proper positioning of insertion by using an adhesive to hold an infusion set in position, and a partially integrated ballistic inserter to insert a needle at a controlled rate of speed to a desired intradermal depth and then release from the set for disposal, thereby reducing an overall size of the device.

BACKGROUND OF THE INVENTION

A large number of people, including those suffering from conditions such as diabetes use some form of infusion therapy, such as daily insulin infusions to maintain close control of their glucose levels. There are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

The use of an infusion pump requires the use of a disposable component, typically referred to as an infusion set or pump set, which conveys the insulin from a reservoir within the pump into the skin of the user. An infusion set typically consists of a pump connector, a length of tubing, and a hub or base from which an infusion needle or cannula extends. The hub or base has an adhesive which retains the base on the skin surface during use, which may be applied to the skin manually or with the aid of a manual or automatic insertion device. Often, a user is further required to carry and provide a separate inserter. Accordingly, this method of treatment can become cumbersome and wasteful when dealing with the large number of required components.

Currently, most insulin infusion sets deliver insulin to the sub-cutaneous layers of skin using either fixed metal needles or flexible plastic cannulas. Such infusion sets typically deliver insulin 4-10 mm below the skin surface. However, the upper 3 mm of skin surface, the intradermal space, facilitates better drug absorption. Unfortunately, due to the relative thinness of the intradermal layer, inserting a needle at such depth and maintaining an infusion site over an extended period of time within this narrow band is difficult.

Further, most insulin infusion sets typically do not provide any features to isolate the inserted needle from shock or other external forces. Since these infusion sets typically deliver insulin 4-10 mm below the skin surface, shock or other external forces to the set have less effect on the deeper inserted needle. However, where an attempt is made to target the upper 3 mm of skin surface, any shock or movement of the set can adversely affect needle insertion and infusion performance.

Still further, as noted above, most insulin sets require separate inserters to provide a lower profile set, but require the user to carry extra components for treatment. However, a fully integrated inserter can result in a device that is too tall, and extends too high above the skin surface. In either case, an additional problem encountered by users of inserters is skin surface "tenting" during needle insertion, where the skin surface is deflected somewhat prior to or during needle insertion which makes precisely targeting the upper 3 mm of skin surface difficult.

Accordingly, a need exists for advanced, improved, and novel components and elements of current and future infusion sets that can deliver content to the upper 3 mm of skin surface, the intradermal space, to facilitate better drug absorption, while maintaining a degree of comfort to the user.

SUMMARY OF THE INVENTION

An object of the present invention is to provide an infusion set which can deliver insulin or other medicament to the upper 3 mm of skin surface, the intradermal space, to facilitate better drug absorption, while maintaining a degree of comfort to the user.

Another object of the present invention is to provide an infusion set having a partially integrated ballistic inserter that can insert a needle at a depth to deliver insulin or other medicament to the upper 3 mm of skin surface.

Another object of the present invention is to provide an infusion set having a partially integrated ballistic inserter that can insert a needle at a controlled high rate of speed to substantially reduce tenting of the skin surface and insert a needle at a depth to deliver insulin or other medicament to the upper 3 mm of skin surface.

Another object of the present invention is to provide an infusion set having a partially integrated ballistic inserter to substantially reduce an overall size of the infusion set.

Another object of the present invention is to provide an infusion set having a removable user contact element such as a turnkey of the partially integrated ballistic inserter that can be provided to release a driving spring of the ballistic inserter to insert a needle at a controlled high rate of speed, of 3.3 ft/sec. (1.0 m/sec.) up to and including those greater than 10 ft/sec. (3.0 m/sec.) then release from the set for disposal, and wherein at least one of the turnkey, fluid connector cover, and base includes an arrow or other mark to aid in infusion set positioning by identifying the final-position, tubing attachment direction.

Another object of the present invention is to provide an infusion set having a removable user contact element such as a pushable handle of the partially integrated ballistic inserter that can be provided to release a driving spring of the ballistic inserter to insert a needle at a controlled high rate of speed, of 3.3 ft/sec. (1.0 m/sec.) up to and including those greater than 10 ft/sec. (3.0 m/sec.) then release from the set for disposal.

Another object of the present invention is to provide an infusion set having a skin securing, adhesive layer to secure the skin surface at the insertion site such that the inserter that can insert a needle with a reduced risk of tenting of the skin surface.

Another object of the present invention is to provide an infusion set that can isolate an inserted needle from external forces such that the needle can be maintained at a depth to deliver insulin or other medicament to the upper 3 mm of skin surface during normal use.

These and other objects are substantially achieved by providing an infusion set having a partially integrated ballistic inserter that can insert a needle at a controlled high rate of speed to a depth to deliver insulin or other medicament to the upper 3 mm of skin surface, and a skin-securing adhesive layer to secure the skin surface at the insertion site such that the inserter that can insert a needle without a risk of tenting of the skin surface. The partially integrated ballistic inserter can include one or more of a pushable insertion handle and a removable turnkey to release a driving spring of the ballistic inserter to insert a needle at a controlled high rate of speed, of 3.3 ft/sec. (1.0 m/sec.) up to and including those greater than 10 ft/sec. (3.0 m/sec.) then release from the set for disposal. Depending upon cannula sharpness, a high terminal velocity produces more reliable results for intradermal insertions of short (i.e., 1.5 mm) needle or cannula. Further, an interface ring can be provided to assist in targeting and delivering content to the upper 3 mm of skin surface, and can then be retracted when the inserter is removed to prevent indentation, edema and erythema.

BRIEF DESCRIPTION OF THE DRAWINGS

The various objects, advantages and novel features of the exemplary embodiments of the present invention will be more readily appreciated from the following detailed description when read in conjunction with the appended drawings, in which.

Throughout the drawings, like reference numerals will be understood to refer to like parts, components and structures.

DETAILED DESCRIPTION OF THE EXEMPLARY EMBODIMENTS

Figure 1:
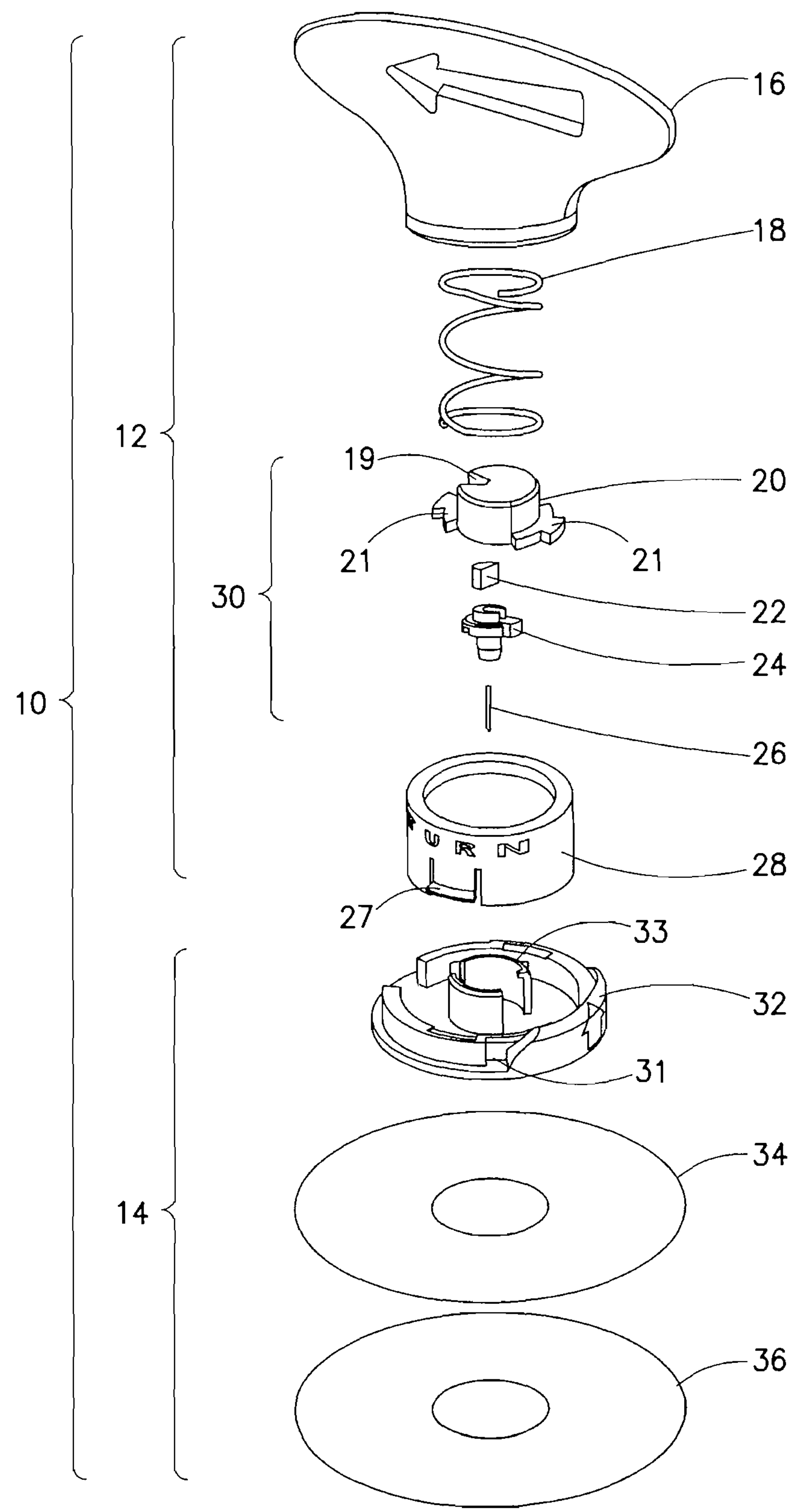
FIG. 1 is an exploded view of a partially integrated turnkey ballistic inserter in accordance with an embodiment of the present invention.

As will be appreciated by one skilled in the art, there are numerous ways of carrying out the examples, improvements and arrangements of insulin-associated devices disclosed herein. Although reference will be made to the exemplary embodiments depicted in the drawings and the following description, the embodiments disclosed herein are not meant to be exhaustive of the various alternative designs and embodiments that are encompassed by the disclosed invention.

The exemplary embodiments of the present invention deliver insulin to the intradermal layer of the skin via a standard insulin pump or other similar device. By utilizing a partially integrated ballistic inserter and a skin securing adhesive, proper insertion and maintenance of the inserted needle in the intradermal space is ensured, while reducing a size of the set and maintaining a degree of comfort to the user.

The exemplary embodiments of the present invention provide an exemplary infusion set having a partially integrated ballistic inserter that can insert a needle at a depth to deliver content to the upper 3 mm of skin surface. To do so, the exemplary embodiments comprise a partially integrated ballistic inserter with a user contact element for activation, that can insert a needle of an infusion set at a controlled high rate of speed to substantially reduce tenting of the skin surface and insert the needle at a depth to deliver content to the upper 3 mm of skin surface when activated. A driving spring of the ballistic inserter is configured to insert a needle at a controlled high rate of speed, of 3.3 ft/sec. (1.0 m/sec.) up to and including those greater than 10 ft/sec. (3.0 m/sec.). Depending upon cannula sharpness, such a terminal velocity produces more reliable results for intradermal insertions of short (i.e., 1.5 mm) needle or cannula with a reduced risk of tenting of the skin surface.

The infusion set is also provided with at least one skin-securing, adhesive layer to secure the infusion set to the skin surface at the insertion site, such that the ballistic inserter when activated by the user is at the correct position relative to the skin surface, and such that the skin is secured during insertion to further aid needle insertion with a reduced risk of tenting of the skin surface.

In each exemplary embodiment of the present invention described below, standard infusion set elements such as connectors, infusion cannula or needles, adhesives and hubs can be provided. A driving spring is provided in an activation subassembly to provide ballistic insertion of the needle. By using such a driving spring, a high-speed insertion is achieved which is considered more reliable for insertion of a short (i.e., 1.5 mm) cannula. Further, after placement and activation, the exemplary embodiments provide means for removing the subassembly, including at least one of the pushable handle and the turnkey, as the user contact element, and driving spring therein, and leaving the plunger subassembly within the infusion set. The set can now receive a fluid connector assembly configured to allow rotation of the infusion set tubing to allow the patient better management of tubing position relative to the pump and provide strain relief from tugging, bumping or other movement that may affect the positioning of the cannula in the skin surface.

In each exemplary embodiment described below, the driving spring can be compressed until it gains a maximum potential energy. This energy is determined by calculating the torsional stresses built up in the driving spring as it is compressed. By calculating potential energy, and the kinetic energy at the point of needle insertion, an insertion velocity can be calculated. In exemplary embodiments of the present invention, the driving spring is configured to insert a needle at a controlled high rate of speed, of 3.3 ft/sec. (1.0 m/sec.) up to and including those greater than 10 ft/sec. (3.0 m/sec.). Depending on cannula sharpness, such a terminal velocity produces more reliable results for intradermal insertions of short (i.e., 1.5 mm) needle or cannula with a reduced risk of tenting of the skin surface. The driving spring diameter, pitch, and material, all contribute to the inherent spring constant. This constant and the total travel of the driving spring once released can be manipulated to produce the desired velocity T.

Figure 2:
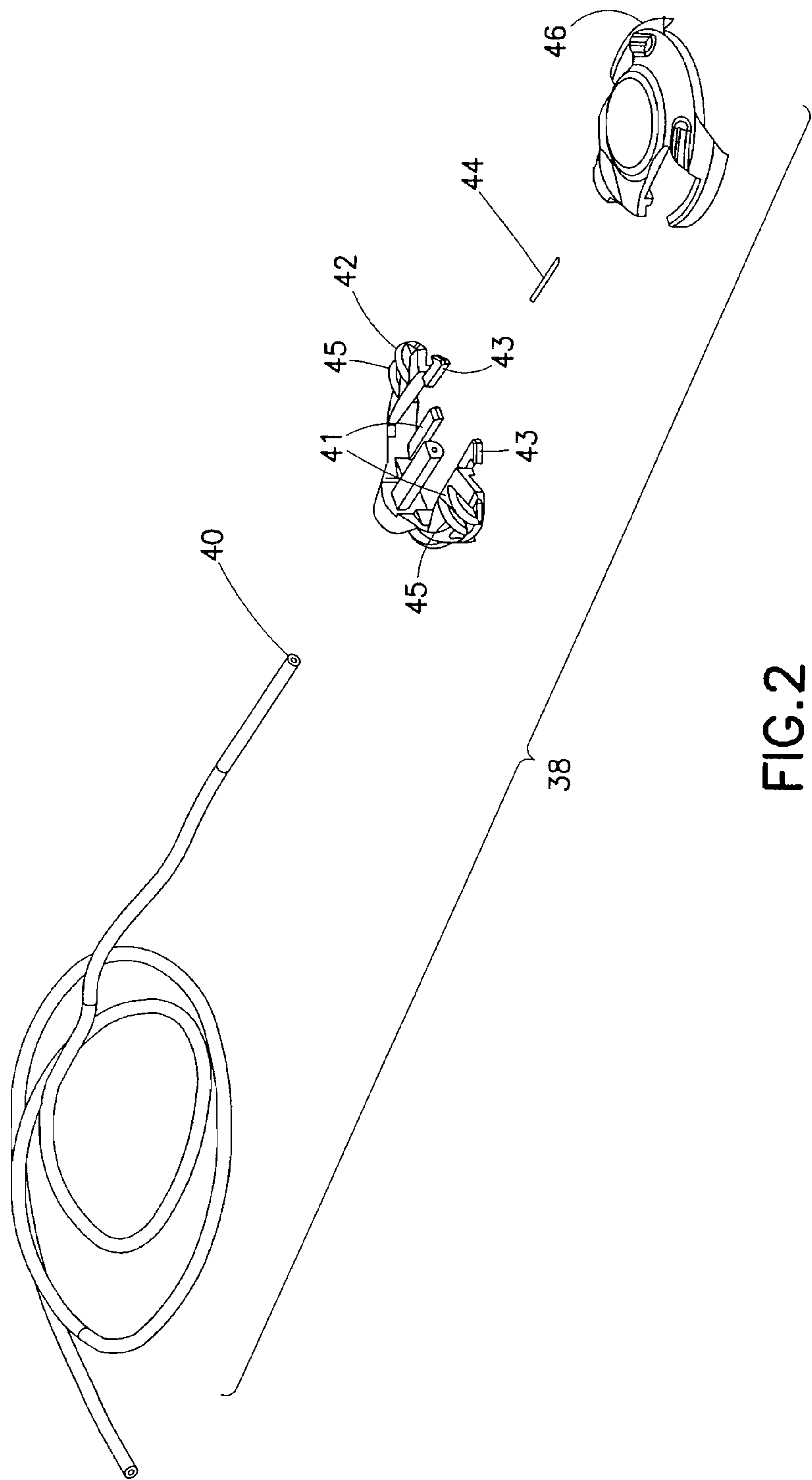
FIG. 2 is an exploded view of a fluid connector assembly in accordance with an embodiment of the present invention.

FIG. 1 is an exploded view of a partially integrated turnkey ballistic inserter in accordance with an embodiment of the present invention, and FIG. 2 is an exploded view of a fluid connector assembly for use with the set of FIG. 1. As shown in FIG. 1, an exemplary pre-activation hub assembly 10 comprises an activation subassembly 12 and a hub base subassembly 14. In exemplary embodiments of the present invention described below, the assemblies and other elements can be constructed of a molded plastic material, polycarbonate, thermoplastic polymer such as polyethylene terephthalate (PET and PETG), or similar materials.

In a first exemplary embodiment, the activation subassembly 12 comprises a thumb-hold turnkey 16, a steel driving spring 18, a plunger bayonet 20, a septum 22, a cannula holder 24, a cannula 26, and an activation key collar 28. Although shown separated in FIG. 1, the user receives the assembled device 10 having the turnkey 16 secured with the activation collar 28 and releasably secured to the hub base subassembly 14, and containing therein plunger 30 and driving spring 18 in a compressed state ready for use. The plunger bayonet 20, septum 22, cannula holder 24, and cannula 26, collectively constitute a septum/cannula subassembly, or plunger 30. The hub base subassembly 14 comprises a base 32, an adhesive 34, and an adhesive backing 36. As shown in FIG. 2, the fluid connector assembly 38 comprises tubing 40, fluid connector slide 42, septum piercing cannula 44, and fluid connector cover 46.

Figure 5:
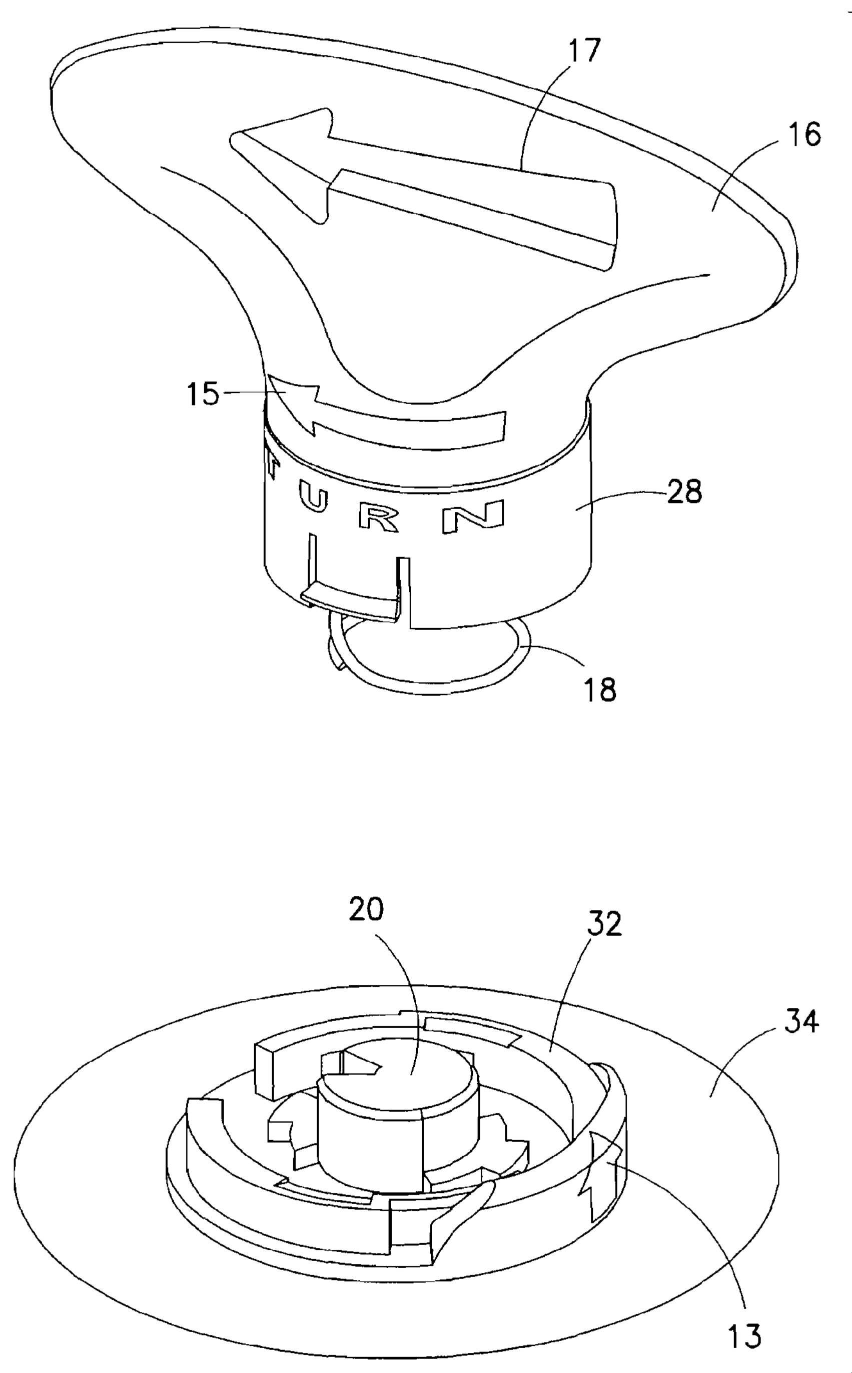
FIG. 5 is an enlarged perspective view of the infusion set and turnkey ballistic inserter after activation and after removal of the activation turnkey subassembly from the hub base in accordance with an embodiment of the present invention.
Figure 8:
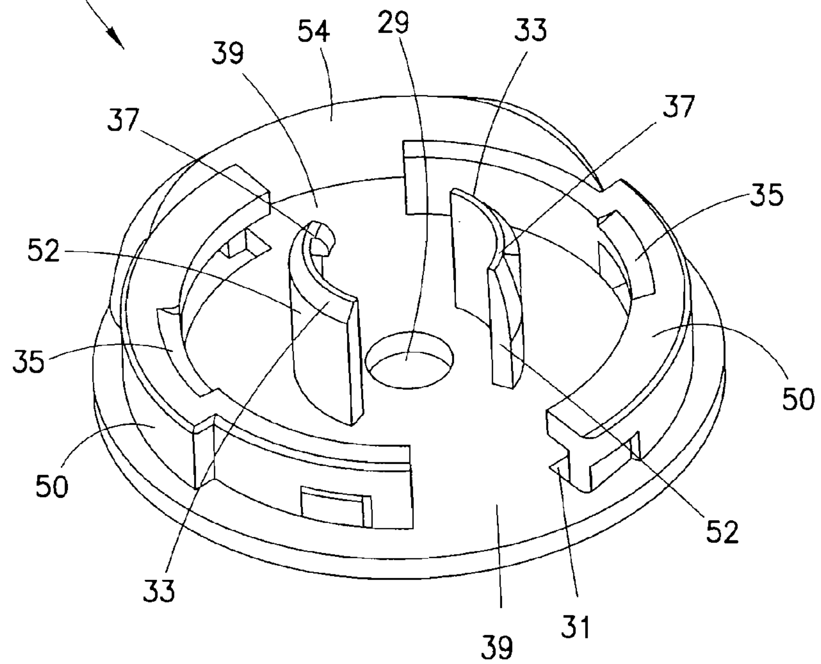
FIG. 8 is an enlarged view of an exemplary base in accordance with an embodiment of the present invention.

The activation subassembly 12 is configured to fit within an upper surface opening of the hub base subassembly 14 shown in greater detail in FIGS. 5 and 8. The driving spring 18 and plunger 30 are captured within the turnkey 16 though interference with one or more detents 47 of the collar 28. Thereafter, turning of the turnkey 16 is used to align openings 49 in the detents 47 with projections of the plunger 30 and with the barrel 33 of the base 32, such that the driving spring 18 can drive the plunger downward and insert the needle into the skin surface. Further turning of the turnkey 16 releases a large part of the activation subassembly 12 from the hub base subassembly 14, while leaving only the plunger 30 in the barrel 33 of the base 32.

Figure 4:
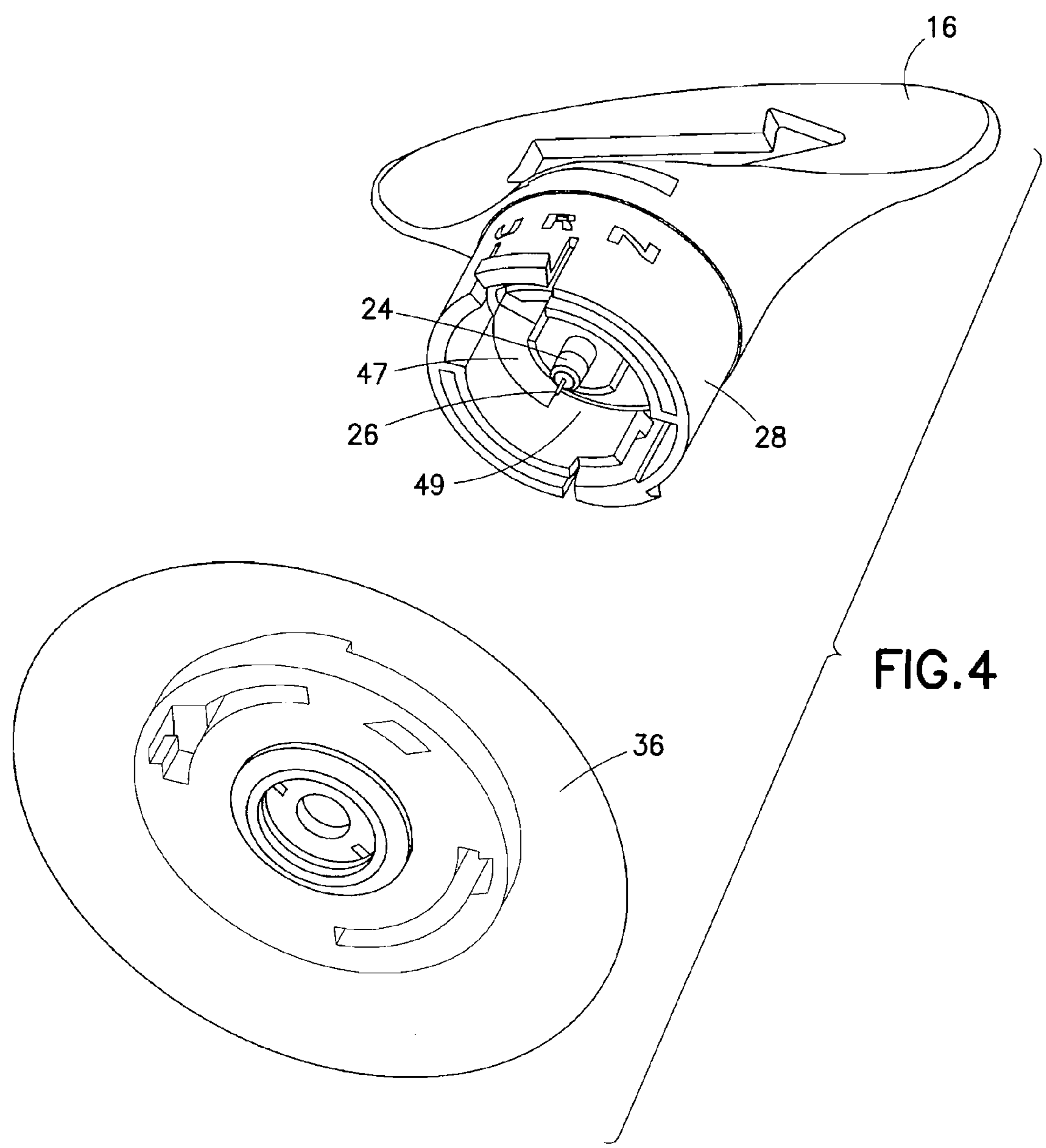
FIG. 4 is an enlarged perspective view of the infusion set and turnkey ballistic inserter before activation and before assembly of the activation turnkey subassembly with the hub base in accordance with an embodiment of the present invention.

As illustrated in FIG. 4, the activation subassembly 12 is assembled into a single upper component, and includes the steel driving spring 18, plunger bayonet 20, septum 22, cannula holder 24, and cannula 26, captured between the thumb-hold turnkey 16 and the activation key collar 28. The driving spring 18 is captured between the turnkey 16 and the plunger bayonet 20 to urge the plunger bayonet 20 and cannula 26 into the skin surface when released. More specifically, the cannula 26 and septum 22 are assembled into the cannula holder 24, which is held in the plunger bayonet 20. The driving spring 18 is configured to have an opening to surround the plunger bayonet 20 and contact one or more projections 21 extending from the plunger bayonet 20. The cannula 26 can preferably comprise a 34 gauge, single-bevel stainless steel needle/cannula, but embodiments are not limited thereto. In yet other embodiments of the present invention, the cannula 26 can be plastic or other material, between 25 gauge and 36 gauge, and provided with a tri-bevel or 5-bevel, and be between 1.0 and 10 mm long, but embodiments are not limited thereto. The cannula 26 can be bonded to the cannula holder 24 with an adhesive, such as a Loctite/UV cured adhesive, or can be over molded with, or threaded into the cannula holder.

The activation collar 28 is provided with one or more snaps 27 to secure the activation collar 28 to snaps 31 of the base 32 during rotation and activation. After activation, the snaps 27 and 31 disengage to allow removal of the turnkey 16, driving spring 18 and collar 28.

The activation collar 28 is also provided with one or more detents 47 to secure the plunger bayonet 20, and is provided with openings 49 in the detents 47 which can be rotated into a position allowing the plunger bayonet 20 or more specifically, the projections 21 of the plunger bayonet 20 to be pushed free of the collar 28. The turning of the turnkey 16 aligns one or more of the openings 49 in the detents 47 of the collar 28 with the projections 21 of the plunger bayonet 20 and with openings in the barrel 33 of the base 32, permitting downward travel of the bayonet 20, septum 22, holder 24 and cannula 26 as urged by the captured driving spring 18. That is, once rotated into position a release position, the driving spring 18 urges the plunger 30 into the base 32 and into the skin surface (not shown) upon which the base 32 is positioned. Further turning of the turnkey 16 disengages the snaps 27 of the activation collar 28 from the snaps 31 of the base to release the key 16, driving spring 18, and collar 28 from the base 32 for removal, thereby leaving a low-profile set adhered to the infusion site.

As shown in the enlarged view of FIG. 8, the base 32 comprises a substantially circular body having extending therefrom a number of features to engage the activation collar 28 and plunger 30. A raised outer ring 50 is provided to engage the activation collar 28, and a raised inner ring 52 is provided to engage the plunger 30. On an opposite side of the base 32, an adhesive layer 34 and removable backing 36 can be provided. The raised outer ring 50 of the base 32 comprises a number of recessed grooves or snaps 31, which terminate at openings 39. An upper surface of the raised outer ring 50 comprises at least two inclined surfaces 35 to allow detents to more easily enter the snaps 31. A raised section 54 is also provided to align the fluid connector cover 46 into proper positioning before the fluid connector slide 42 is engaged. The raised inner ring 52 of the base 32 surrounds an opening 29 in the base 32 and comprises the barrel 33 into which the plunger 30 is driven when released by the turnkey 16. One or more latches 37 are provided on the barrel 33 to securely hold the plunger 30 in position within the barrel once the turnkey, driving spring and collar are removed.

FIG. 8 also illustrates the connection features provided for engagement between snaps 27 of the activation collar 28 and snaps 31 of the base 32. Specifically, the snaps 27 are provided as deflectable arms with inclined ramps at ends thereof. As the inclined ramps engage similar inclines 35 of the base 32, the snaps 27 are deflected until falling into place in groove 31. In such a position, the activation subassembly 12 is rotatably secured to the hub base subassembly 14. The assembly of the activation subassembly 12 and the hub base subassembly 14 is performed in a straight-line motion, preferably at the time of manufacture of the device. Once the device is adhered to a skin surface and activated by turning the turnkey 16, further turning of the turnkey 16 results in the snaps 27 of the activation collar 28 reaching the openings 39 which releases the snaps 27, thereby releasing the activation collar 28, turnkey 16, and driving spring 18, while leaving the plunger 30 held within the barrel 33 by the base snaps 37.

However, if there is a misalignment of the plunger 30 with the barrel 33 or other failure such that proper insertion does not occur, the snaps 27 are prevented from reaching the openings 39 (i.e., complete turnkey rotation is prevented) such that the turnkey 16, driving spring 18 and activation collar 28 remain secured to the base 32. The turnkey rotation in this case can be prevented by providing one or more interference ribs (not shown) within the activation collar 28 to contact, for example, the projections 21 extending from the plunger bayonet 20. Such projections 21 move with the bayonet 20 during proper placement, and therefore, if out of place, indicate improper placement. In this case the entire device is removed and replaced with a new device.

Figure 3:
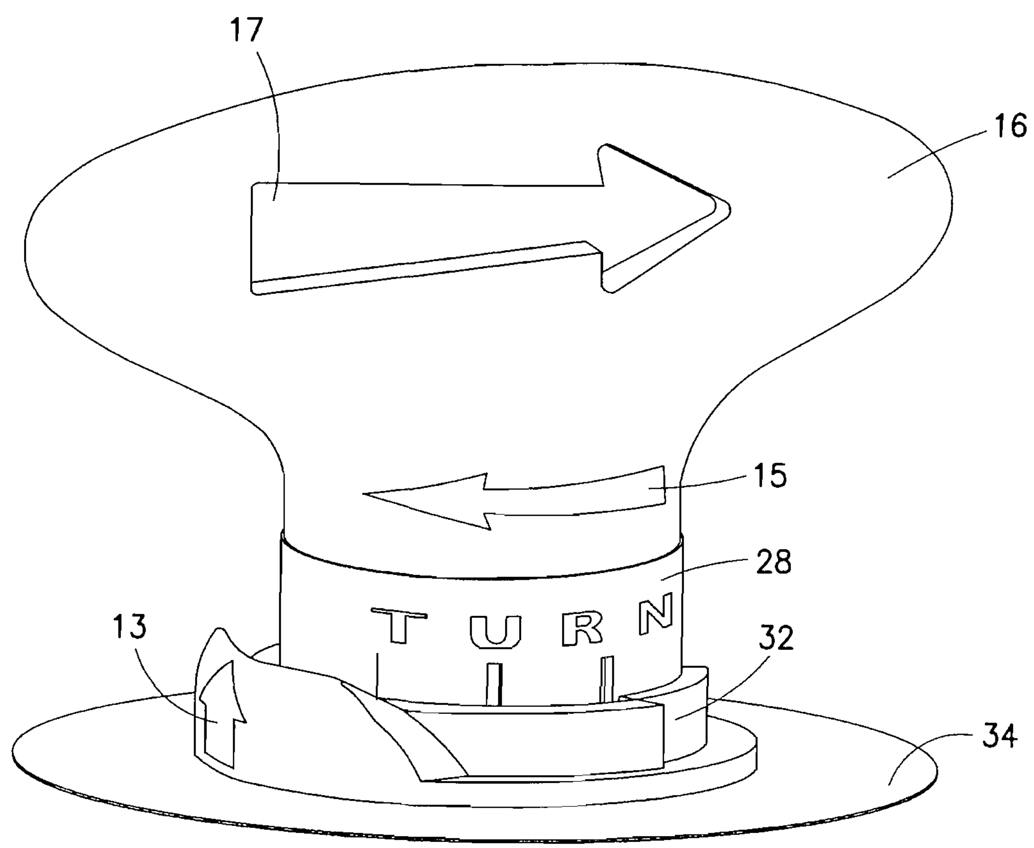
FIG. 3 is an enlarged perspective view of the assembled infusion set and turnkey ballistic inserter before activation in accordance with an embodiment of the present invention.

FIGS. 3-7 are enlarged perspective views of an assembled infusion set and ballistic inserter in use in accordance with an embodiment of the present invention. FIG. 4 is provided to illustrate a separated activation subassembly 12 and hub base subassembly 14. However, in an exemplary embodiment of the present invention, the user receives an assembled device as shown in FIG. 3 wherein the activation subassembly 12 is releasably secured with the hub base subassembly 14. That is, the user receives the assembled device 10 having the turnkey 16 secured with the activation collar 28 and releasably secured to the hub base subassembly 14, and containing therein plunger 30 and driving spring 18 in a compressed state ready for use. The user is not required to compress the driving spring 18.

Before the set is activated, the backing 36 of adhesive layer 34 is removed and the device is placed on a skin surface. At least one of the turnkey 16, fluid connector cover 46, collar 28 and base 32 includes an arrow or other mark to aid in infusion set positioning by identifying the turning direction of the turnkey, and the final-position, tubing attachment direction. As shown by the assembled device of FIG. 3 that is ready for application to an insertion site, the turnkey 16 can be marked with an arrow 17 and the base 32 can be marked with an arrow 13 that both point in the direction of the final-position, tubing 40 attachment direction. Further, the turnkey 16 can be marked with an arrow 11 for alignment with the arrow 13 of the base 32 during cover assembly with the base and for denoting a turning direction of the turnkey 16 during use to ensure proper activation and release of the activation subassembly 12.

Accordingly, once the backing 36 of the adhesive layer 34 is removed and the device is oriented for desired tubing 40 attachment direction and placed on a skin surface, the user then grips and turns the thumb-hold part, or turnkey 16, to activate the device. The plunger 30 is released by bayonet action allowing the plunger to be pushed down by the driving spring 18 and locked in place by the retention snaps 37 of the base 32. The cannula 26 is thereby inserted into the dermis, and preferably, into the upper 3 mm of skin surface, the intradermal space, to facilitate better drug absorption and is held in place by the retention snaps 37 of the base 32. The plunger 30 remains on the base 32 and the turnkey, driving spring and activation collar are removed to be discarded as shown in FIG. 5. Interference ribs on the turnkey prevent the key from releasing if the plunger 30 is not in the correct post-activation position. This prevents the user from attempting to connect the device after partial or failed activation.

Figure 6:
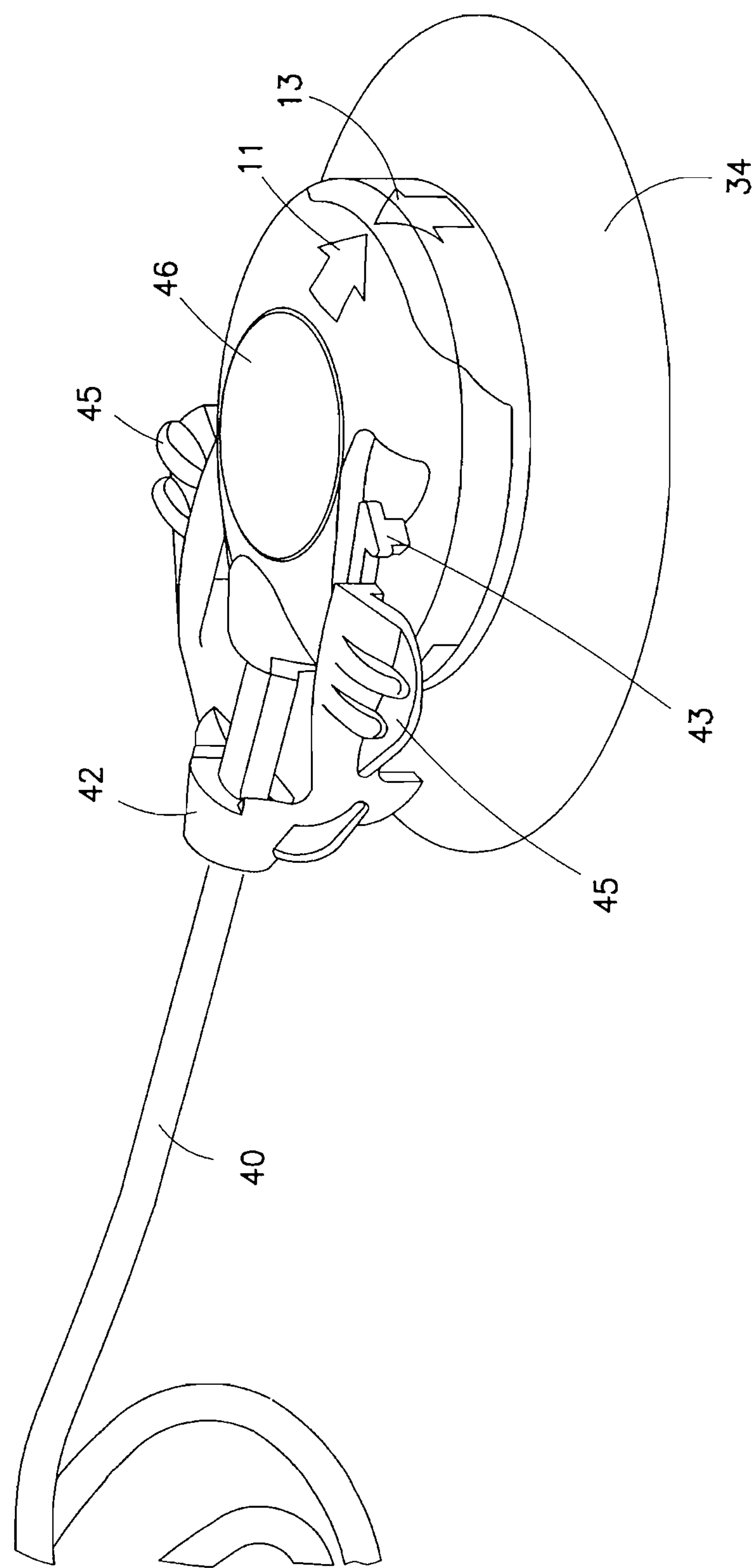
FIG. 6 is an enlarged perspective view of an assembled infusion set and fluid connector assembly in accordance with an embodiment of the present invention.
Figure 7:
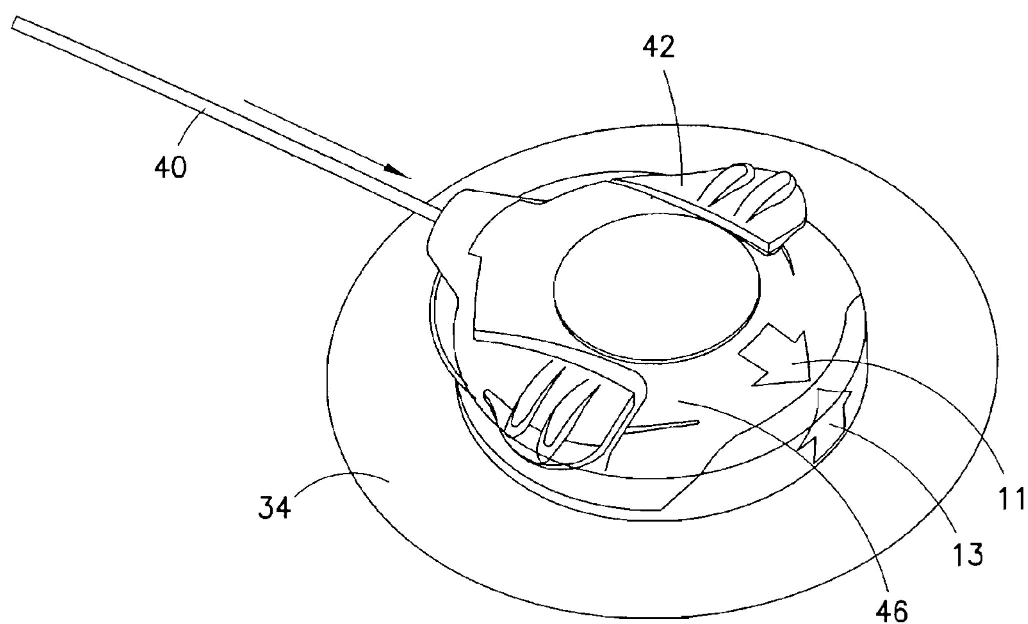
FIG. 7 is an enlarged perspective view of an assembled infusion set and fluid connector assembly wherein the fluid connector slide is in a final position in accordance with an embodiment of the present invention.

The fluid connector assembly 38 can then be positioned over the set as shown in FIG. 6, and the fluid connector slide 42 can be pressed inward to complete attachment as shown in FIG. 7. As shown in FIG. 2, the fluid connector assembly 38 comprises tubing 40, fluid connector slide 42, septum piercing cannula 44, and fluid connector cover 46. The fluid connector slide 42 is slidably captured within the fluid connector cover 46. When the plunger 30 is properly positioned within the barrel 33 of the base 32, the alignment recess 19 of the plunger 30 is positioned to receive the piercing cannula 44 of the slide into the septum 22. The fluid connector slide 42 is pressed inward such that the septum-piercing cannula 44 pierces the septum 22 of the plunger 30, completing the fluid path, and locking the fluid connector 46 to the base 32.

The user can attach the fluid connector assembly 38 to the set by aligning the arrows 15 and 13 on the fluid connector cover 46 and the base 32, respectively, and placing the fluid connector cover 46 over the base 32. The raised section 54 is also provided to align the fluid connector cover 46 into proper positioning before the fluid connector slide 42 is engaged. Pressing the fluid connector slide 42 inward then serves to lock detents of the arms 43 of the fluid connector slide 42 to detents within the cover 46, and serves to lock interference arms 41 to similarly shaped receiving openings in the raised outer ring 50 of the base 32. The interference arms 41 also serve to prevent the fluid connector slide 42 from moving into the fluid connector cover 46 if the fluid connector cover 46 is not properly seated to prevent incorrect connection or damage to the piercing cannula 44. The bayonet 20 provides the alignment recess 19 to receive the piercing cannula 44 of the slide into the septum 22 thereby completing the connection. The fluid connector assembly 38 can be removed by pinching the grips 45 of the connector slide 42 to deflect the aims 43 of the slide and disengage the detents of the arms 43 from the detents of the fluid connector cover 46. After pinching the grips 45, the user can pull back the fluid connector slide 42 until slide travel reaches a positive stop, and lift the fluid connector cover 46 from the base 32.

In yet another exemplary embodiment of the present invention, the activation subassembly can comprise a pushable activation subassembly. The following embodiments provide an exemplary infusion set having another partially integrated ballistic inserter that can insert a needle at a depth to deliver content to the upper 3 mm of skin surface. To do so, the exemplary embodiments comprise a partially integrated ballistic inserter that can again insert a needle of an infusion set at a controlled high rate of speed to substantially reduce tenting of the skin surface and insert the needle at a depth to deliver content to the upper 3 mm of skin surface. A driving spring of the ballistic inserter is again configured to insert a needle at a controlled high rate of speed, of 3.3 ft/sec. (1.0 m/sec.) up to and including those greater than 10 ft/sec. (3.0 m/sec.). Depending on cannula sharpness, such a terminal velocity produces more reliable results for intradermal insertions of short (i.e., 1.5 mm) needle or cannula with a reduced risk of tenting of the skin surface.

Figure 9:
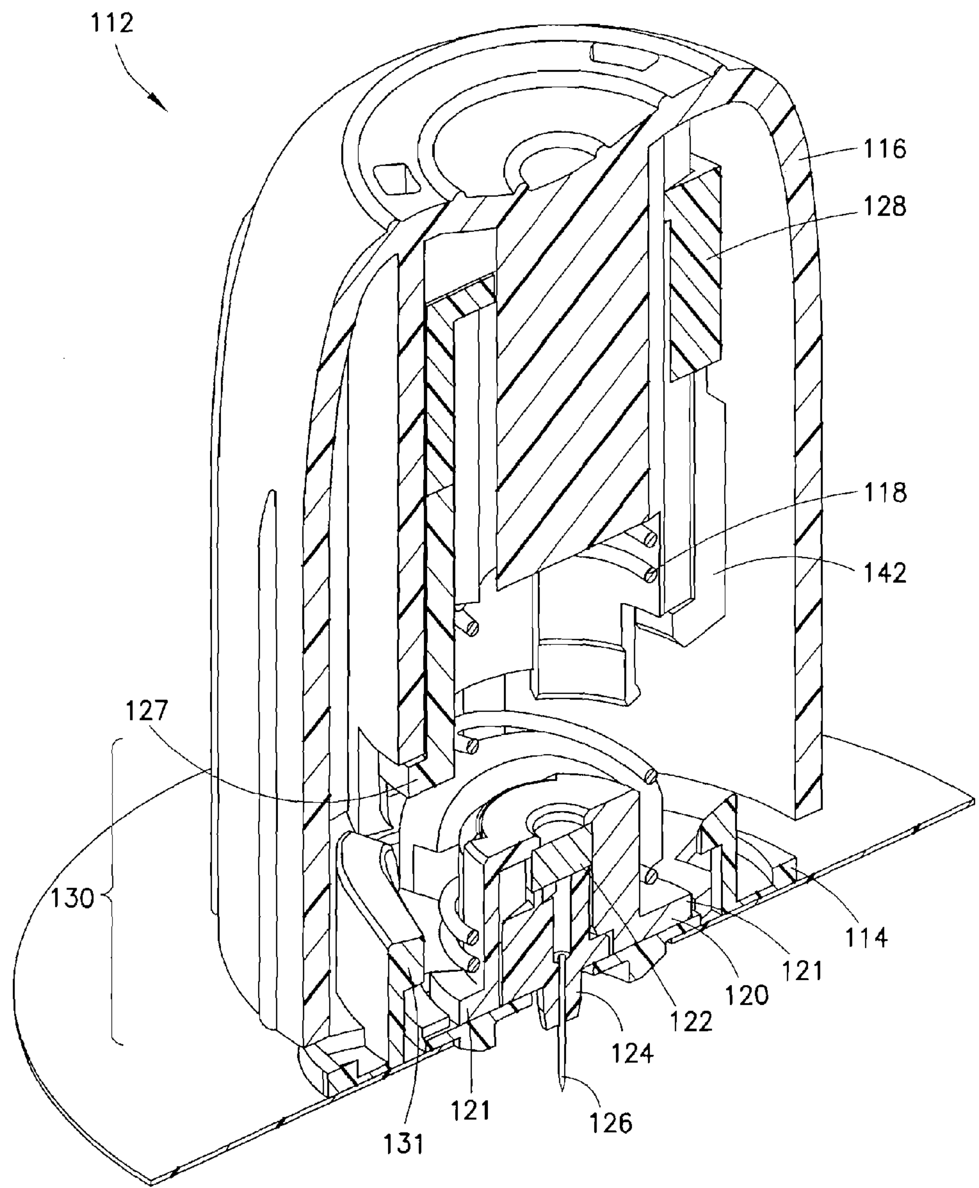
FIG. 9 is an enlarged sectional view of a partially integrated pushable ballistic inserter in accordance with another embodiment of the present invention.
Figure 10:
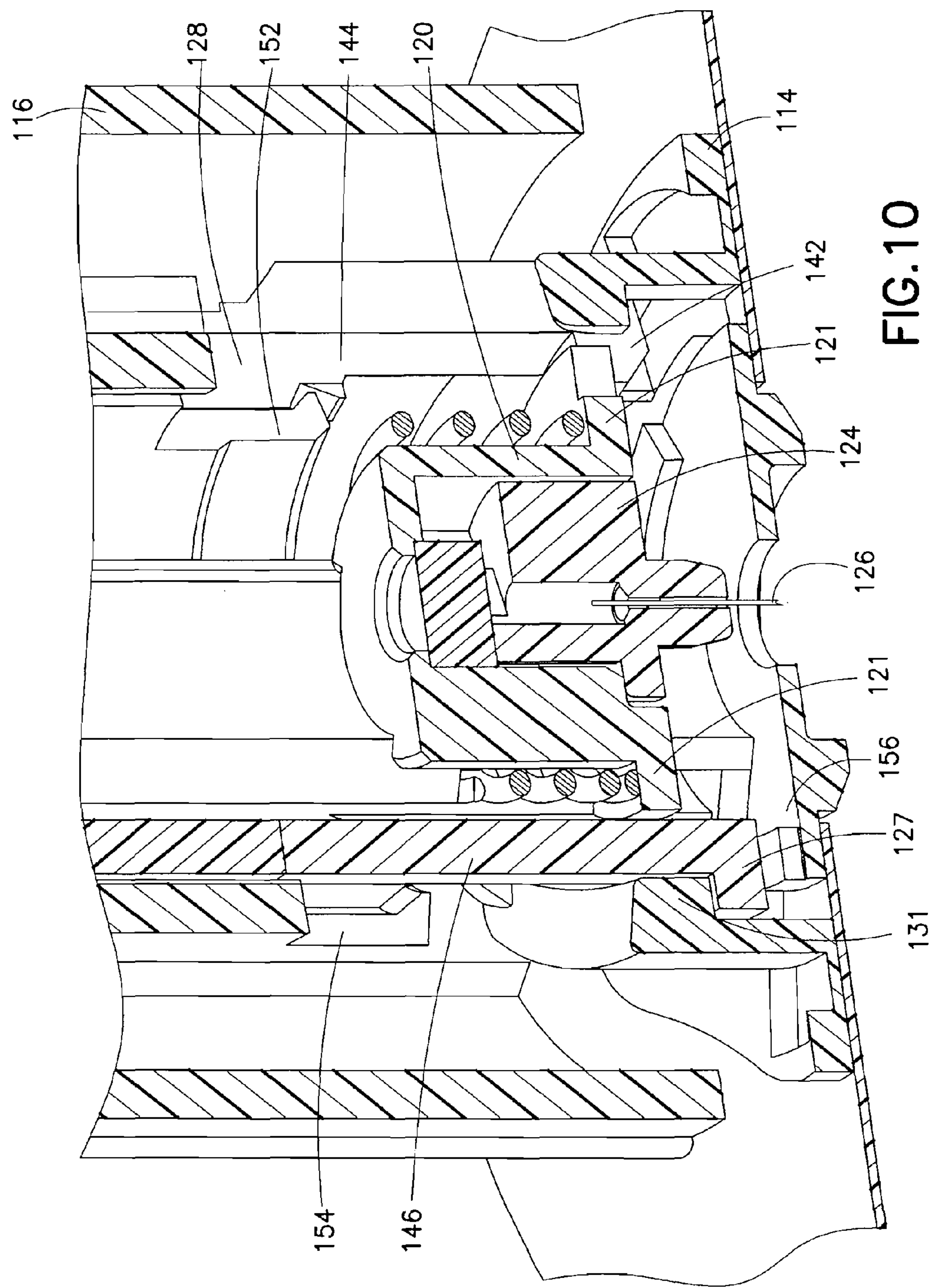
FIG. 10 is an enlarged sectional view of an assembled infusion set and pushable insertion handle ballistic inserter before activation in accordance with an embodiment of the present invention.
Figure 11:
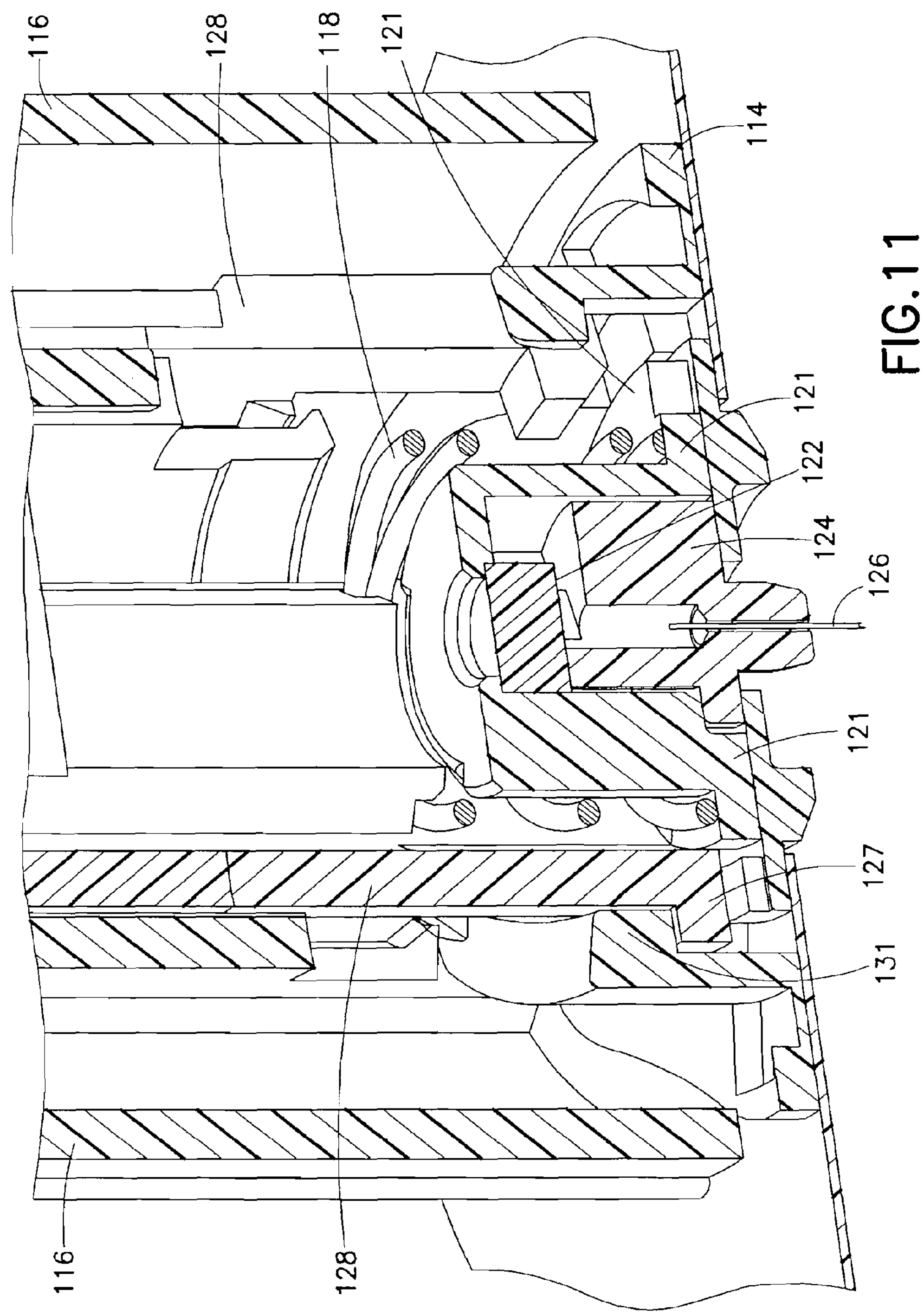
FIG. 11 is an enlarged sectional view of an assembled infusion set and pushable insertion handle ballistic inserter after activation and before release of the insertion handle in accordance with an embodiment of the present invention.
Figure 12:
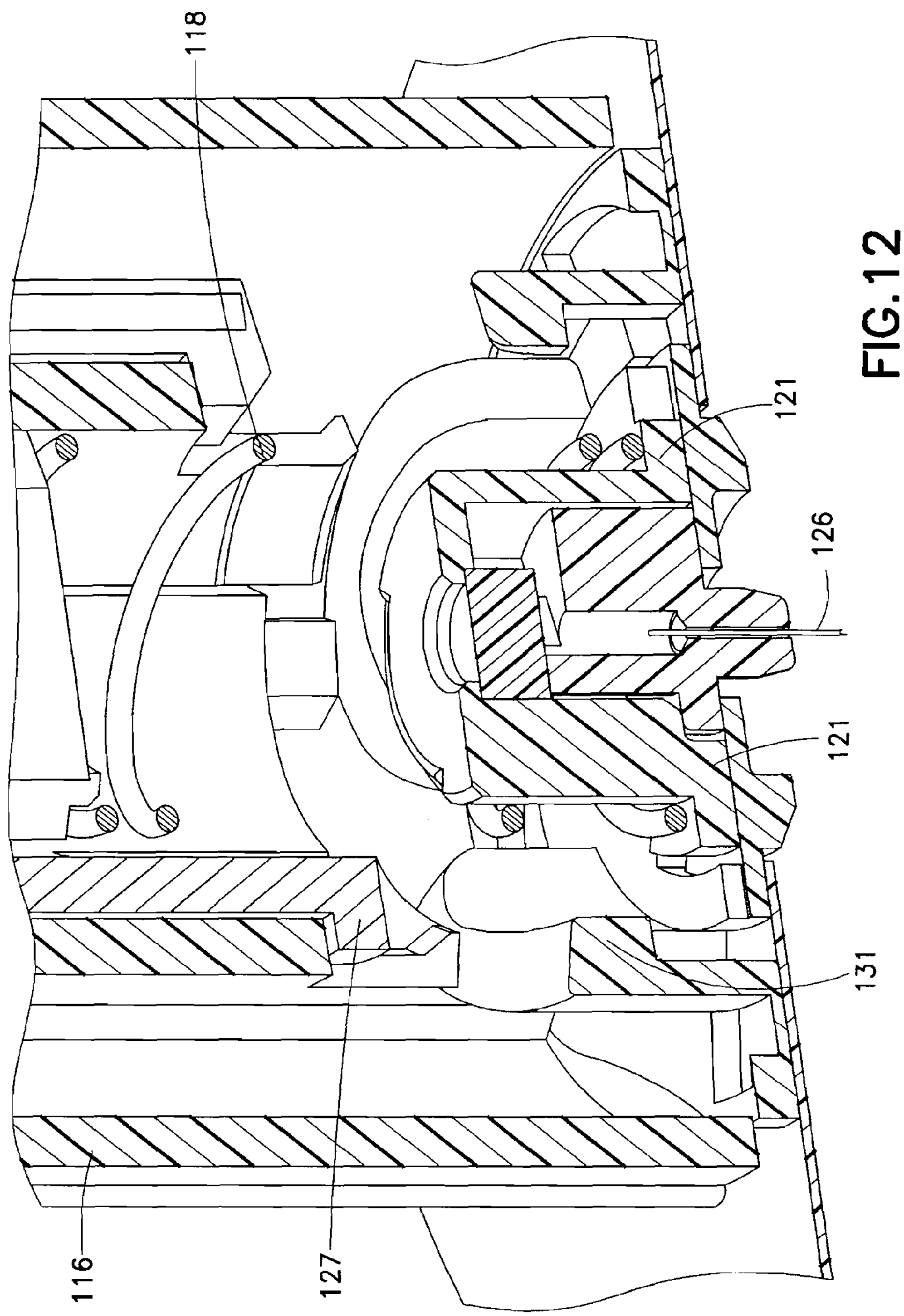
FIG. 12 is an enlarged sectional view of an assembled infusion set and pushable insertion handle ballistic inserter after release of the insertion handle in accordance with an embodiment of the present invention.

FIG. 9 is an enlarged sectional view of a partially integrated pushable ballistic inserter in accordance with the second embodiment of the present invention, and FIGS. 10-12 are enlarged sectional views of an assembled infusion set and pushable insertion handle ballistic inserter before activation, after activation and before release, and after release of the insertion handle.

In the second exemplary embodiment, the activation subassembly 112 comprises a pushable handle 116, a steel driving spring 118, a plunger bayonet 120, a septum 122, a cannula holder 124, a cannula 126, and an inserter base 128. The plunger bayonet 120, septum 122, cannula holder 124, and cannula 126, collectively constitute a septum/cannula subassembly, or plunger 130. The hub base 114 is substantially as described above with the elimination of the raised inner ring 52.

The activation subassembly 112 is configured to fit upon an upper surface of the hub base subassembly 114. Thereafter, pressing downward of the handle 116 is used release the plunger 130 such that the driving spring 118 can drive the plunger 130 downward, and insert the needle 126 into the skin surface (not shown). Further pressing of the handle 116 releases the inserter base 128 which is urged upward into the handle 116 by the remaining tension of the driving spring 118, and releases a large part of the activation subassembly 112 from the hub base 114, while leaving only the plunger 130 in the base 114. The user receives the assembled device having the activation subassembly 112 releasably secured to the hub base subassembly 114, and containing therein plunger 130 in an up position and the driving spring 118 in a compressed state between the inserter base 128 and the plunger 130 ready for use. The user is not required to compress the driving spring 118.

As illustrated in FIG. 10, the activation subassembly 112 is assembled into a single upper component, and includes the steel driving spring 118, plunger bayonet 120, septum 122, cannula holder 124, cannula 126, and the inserter base 128, captured between the handle 116 and the base 114. The driving spring 118 is captured between the inserter base 128 and the plunger bayonet 120 to urge the plunger bayonet 120 and cannula 126 into the skin surface when released. More specifically, the cannula 126 and septum 122 are assembled into the cannula holder 124, which is held in the plunger bayonet 120. The driving spring 118 is configured to have an opening to surround the plunger bayonet 120 and contact one or more projections 121 extending from the plunger bayonet 120. The cannula 126 can preferably comprise a 34 gauge, single-bevel stainless steel needle/cannula, but embodiments are not limited thereto. In yet other embodiments of the present invention, the cannula 126 can be plastic or other material, between 25 gauge and 36 gauge, and provided with a tri-bevel or 5-bevel, and be between 1.0 and 10 mm long, but embodiments are not limited thereto. The cannula 126 can be bonded to the cannula holder 124 with an adhesive, such as a Loctite/UV cured adhesive, or can be over molded with, or threaded into the cannula holder.

The inserter base 128 is provided with one or more snaps 127 extending outwardly to secure the inserter base 128 to snaps 131 of the base 132 and hold the driving spring 118 in a compressed state against the plunger bayonet 120. After activation, the snaps 127 and 131 disengage to allow removal of the handle 116, driving spring 118 and inserter base 128.

In a first stage shown in FIG. 10, the assembled device is shown. Specifically, FIG. 10 is an enlarged sectional view of the assembled infusion set and pushable insertion handle ballistic inserter as received by the user and before activation. As shown in FIG. 10, the handle 116 is pushably secured to the inserter base 128, and the inserter base 128 is releasably secured to the base 114 and holding the driving spring 118 in a compressed state against the plunger bayonet 120. The driving spring 118 is captured between the inserter base 128 and the plunger bayonet 120, which is held from travel by arm 142 of the inserter base 128.

In a second stage, the arm 142 of the inserter base 128 is deflected from the plunger bayonet 120 by contact between the downward moving handle 116 contacting an arm 144 of the inserter base 128. The deflection of the arm 144 of the inserter base 128 by the handle 116 deflects the arm 142 of the inserter base 128 and releases the plunger bayonet 120. The plunger bayonet 120 is then urged downward into final skin-contact position by the driving spring 118 as shown in FIG. 11.

In a third stage, the snaps 127 of the inserter base 128 are deflected from the snaps 131 of the base 114 by further contact between the downward moving handle 116 contacting an arm 146 of the inserter base 128. The deflection of the arm 146 of the inserter base 128 by the handle 116 deflects the snaps 127 from the snaps 131, and releases the inserter base 128 from the base 114. The inserter base 128 is then urged upward into final position by the remaining force of the driving spring 118 as shown in FIG. 12 to allow removal of the handle 116, driving spring 118 and inserter base 128. Further, the driving spring is configured to extend no further than the handle 116 cavity when relaxed, such that no portion of the driving spring 118 extends beyond the handle 116 when the handle 116 is removed.

In this embodiment, the pushable handle activation subassembly releases after activation and can be disposed. The driving spring 118 is contained in the activation handle 116, retracts and is captured during insertion so it does not protrude from the handle 116 after cannula insertion. The fluid connector for this embodiment can be provided substantially as described above.

In an exemplary application of such an embodiment, an adhesive cover can be removed and the device can be placed on the desired location. The device is adhered to the skin during this step. The pushable handle is pressed down in one motion, which performs at least the two following actions. First, features such as ribs 152 in the pushable handle 116 press out arms 144 that hold the driving spring loaded septum/cannula plunger 130. This inserts the cannula into the skin. Second, different features, such as ribs 154 in the pushable handle 116, interfere with arms 146 that secure the disposable part to the infusion set base pushing the arms in, releasing the inserter base 128 from the infusion set base. When these arms are free, the driving spring 118, which at this point is still partially compressed, pushes the inserter base 128 and the driving spring 118 up into the pushable handle 116 where it is captured. Pushing the inserter base 128 and the driving spring 118 into the pushable handle 116 prevents the inserter base 128 from reattaching to the infusion set base after activation and hides the driving spring 118 in the pushable handle 116. At this point, the disposable portion is free and can be thrown away.

The pushable handle 116 has an interference rib that prevents the handle 116 from moving into the base release position if the plunger has jammed. For example, the projections

121 extending from the plunger bayonet 120 interfere with the snaps 127 when trying to disengage from the snaps 131. Once the plunger is properly positioned, the projections 121 extending from the plunger bayonet 120 can occupy spaces 156 to thereby no longer interfere with the snaps 127 when trying to disengage from the snaps 131. This prevents the user from removing the disposable portion and connecting the device if the needle is not in the inserted position. The inserter base retention and interference features are cyclically spaced to allow the part to be two-piece molded. The features are cyclically spaced to prevent undercuts that would prevent the part from being two-piece moldable.

Figure 13A:
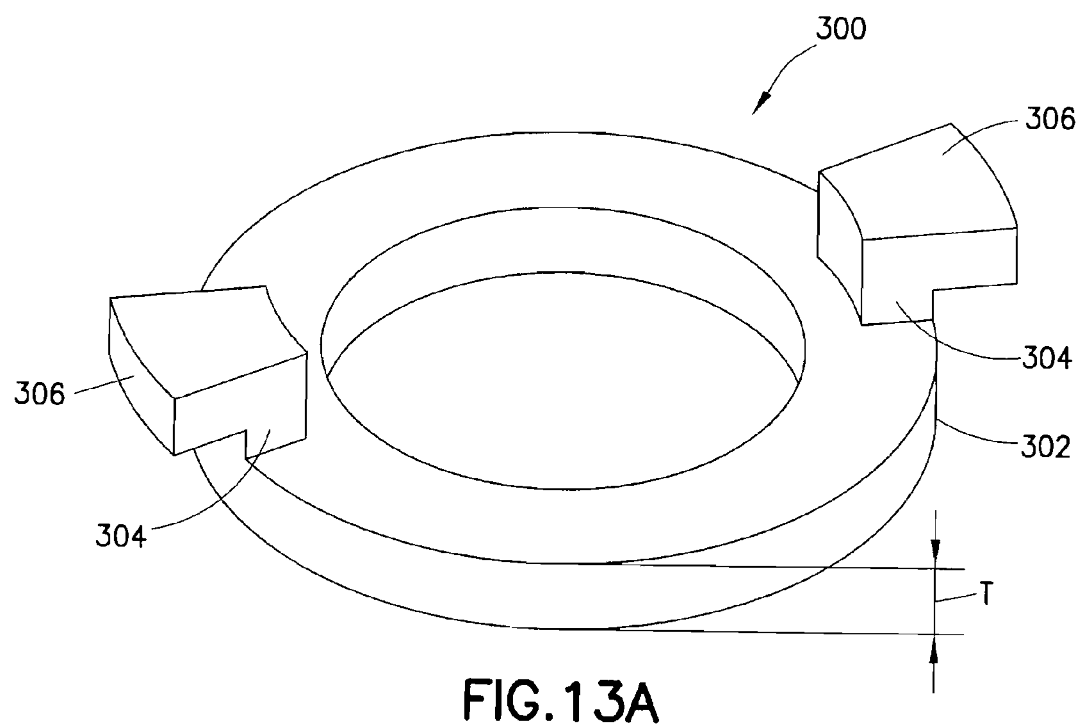
FIG. 13A is a perspective view of a retractable interface ring in accordance with another embodiment of the present invention.
Figure 13B:
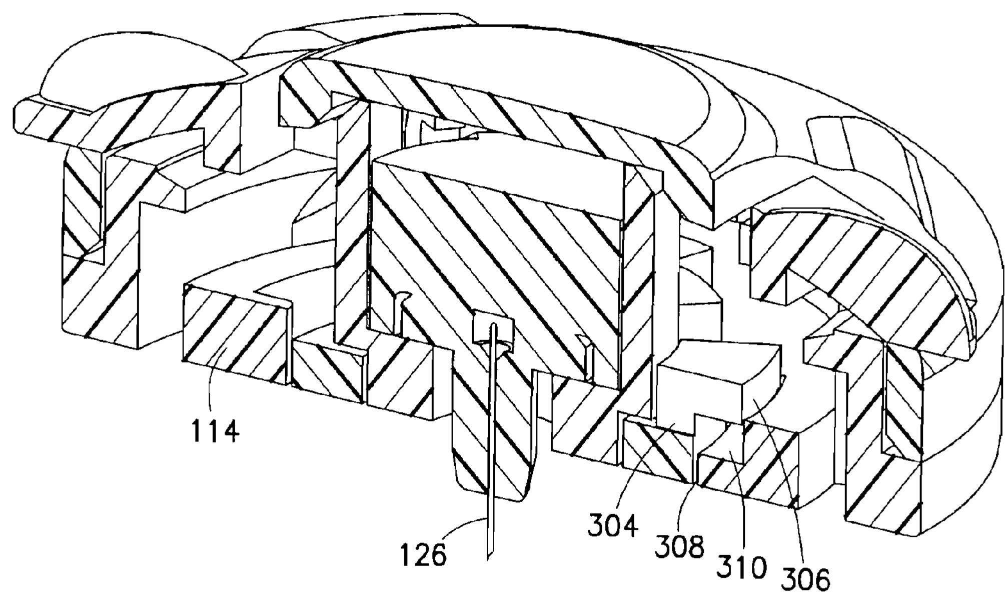
FIG. 13B is a sectional view showing the retractable interface ring of FIG. 13A installed with an infusion set.

Each exemplary embodiment described above can further include one or more features to aid in the targeting and delivery of content to the upper 3 mm of skin surface, the intradermal space, to facilitate better drug absorption, while maintaining a degree of comfort to the user. For example, a skin contact surface of the devices can further comprise a feature or element to manipulate the skin in a way that allows the needle to penetrate into the skin rather than tenting the skin. Such a feature or elements can be provided for insertion of the needle, but may not be required for retention. FIG. 13A is a perspective view of a retractable interface ring in accordance with another embodiment of the present invention, and FIG. 13B is a sectional view showing the retractable interface ring installed with an infusion set.

As shown in FIG. 13A, the retractable interface ring 300 comprises a circular body 302 with a center opening to surround an infusion site as described in greater detail below. The body 302 is provided with at least two leg members 304 having a shoulder 306 disposed at ends thereof. The members 304 and shoulders 306 are configured to enter openings 308 in a bottom surface of the base 114. When the body 302 is rotated, the members 304 and shoulders 306 become slidably captured with the openings 308 in the bottom surface of the base 114. That is, the retractable interface ring 300 is configured to be extendable from the base 114 as provided by the space 310. In an exemplary embodiment, the interface ring comprises a thickness T of between 0.010 and 0.015 inches, and preferably a thickness T of 0.013 inches, but embodiments are not limited thereto.

For example, the shoulders 306 of the ring 300 are configured to contact the snaps 127 of the inserter base 128 when the inserter base 128 is secured to the base during activation. This contact urges the ring 300 into a position extended from the base 114 during placement and activation. Upon release and removal of the turnkey or pushable handle inserter, such contact is removed and the ring 300 is pushed into a flush position with the bottom surface of the base 114 by the tension of the skin contact surface. In doing so, prolonged positioning of the device on the skin surface does not result in extended ring effects.

In a conventional system, any feature protruding from the base of the hub into the skin of the user can leave a temporary indentation in the skin and can cause irritation. However, the exemplary embodiment shown in FIGS. 13A and 13B provides an interface ring that is present during insertion, but is then retracted when the inserter is removed to prevent indentation, edema and erythema. The embodiment can be applied to any integrated insertion infusion set that releases the hub base after activation. In the exemplary embodiment shown, the device comprises a ring; however in this or other exemplary embodiments, the device can comprise a ring and a cone, to target and deliver content to the upper 3 mm of skin surface by, for example, aiding in the insertion of a microneedle 1.5 mm into the dermal layer. The embodiment manipulates the skin in a way that allows such a microneedle to penetrate into the skin rather than tenting the skin. In at least one implementation, the embodiment is configured to be provided for insertion of the needle, but not retention. Further, as a simple element that can be assembled with the base, the ring is part of the hub, so it remains in place for the entire duration the device is worn.

To implement this requires only one additional part, the ring, that can be created with a two-piece injection mold, therefore, there is minimal additional molding. The part is assembled by inserting and rotating the part into the infusion set hub, therefore, there is minimal additional assembly. During activation of the infusion set, the inserter is attached to the hub base and maintains the interface ring in its distal position protruding into the skin. When the inserter is removed, the elasticity pushes the interface ring to its proximal position which is flush with the base of the hub.

As noted above, the driving spring is configured to insert a needle at a controlled high rate of speed, of 3.3 ft/sec. (1.0 m/sec.) up to and including those greater than 10 ft/sec. (3.0 m/sec.). Depending on cannula sharpness, such a terminal velocity produces more reliable results for intradermal insertions of short (i.e., 1.5 mm) needle or cannula. The driving spring diameter, pitch, and material all contribute to the driving spring constant. This constant and the total travel of the spring once released can be manipulated to produce the desired velocity T.

Although the exemplary embodiments described above are preferably used for intradermal injections, each can also be used for subcutaneous injections. Further, one or more of the exemplary embodiments of the present invention can be provided with a skin-contacting adhesive layer and backing. Precise insertion therefore, can be further ensured by first securing the infusion set to the infusion site via the adhesive, which permits the user to activate the partially integrated ballistic inserter at the proper alignment and insert the needle. In doing so, the needle is driven into the skin surface at a controlled high rate of speed to minimize the risk of tenting at needle insertion. Further, the adhesive at or very near the insertion site secures the skin surface and further minimizes tenting of the skin surface during insertion.

In an exemplary use of the embodiments of the present invention, proper insertion of the infusion set into the delivery site consists of straightforward steps. For example, a backing is peeled off the skin adhesive layer of the infusion set, and the infusion set is adhered to the skin surface in the area of the desired infusion site. The user then turns the key or presses the pushable handle to release the driving spring, inserting the needle into the skin surface of the infusion site, and further turns the key or further presses the pushable handle to remove the key or handle, driving spring and collar, while leaving the septum/cannula subassembly plunger in the base of the set. The user can then attach the tube set connection to the septum/cannula subassembly plunger now secured within the base of the set, then prime the infusion set, and deliver medicament to the infusion site via the attached infusion pump (not shown).

Further, the partially integrated ballistic inserter and set ensure proper alignment and positioning. Most inserters on the market are either oversized, to ensure an insertion force perpendicular to the skin surface, or are thin and portable, which can lead to misaligned insertion. In the exemplary embodiments of the present invention, by first adhering or "locking" the outer skin adhesive of the infusion set to the skin surface, the ballistic inserter is aligned properly for needle insertion.

Such a system and method further allows the use of a small intradermal needle (i.e., 34G), or microneedle, which can be placed perpendicular to the skin surface, and which is isolated from outside forces, thereby maintaining position and causing less pain to the user during use. Still further, by infusing medicament into the intradermal layer of the skin, the exemplary embodiments of the present invention offer the potential for better absorption of the insulin when compared to subcutaneous delivery systems. In doing so, it may be possible for the typical user to both consume less insulin and maintain a better medicament regime. It will be appreciated that multiple needles or microneedles can be used, if desired, in place of a single needle or microneedle.

As noted above, other intradermal infusion set concepts are at risk of tenting, which is the undesired effect where skin is deflected at or during insertion, creating a shape associated with a tent. In doing so, the skin surface tents during needle insertion rather than needle penetration into the skin. However, since the present invention provides a needle which is inserted at a controlled high rate of speed, of 3.3 ft/sec. (1.0 m/sec.) up to and including those greater than 10 ft/sec. (3.0 m/sec.), and wherein the skin surface is secured at the insertion site, the exemplary embodiments of the present invention reduce this risk and ensure more precise needle insertion depth. That is, the needle is inserted at a controlled high rate of speed, of 3.3 ft/sec. (1.0 m/sec.) up to and including those greater than 10 ft/sec. (3.0 m/sec.), which does not give the skin time to tent. The reaction of the skin relative to the insertion speed of the needle prevents tenting from adversely affecting final needle depth, such that a more accurate depth can be reached. Further, since the skin does not tent, a much shallower depth can be targeted. Still further, since the skin surface is secured at the insertion site via one or more adhesive layers, the secured skin is even further prevented from tenting such that a much shallower depth can be targeted. To maintain the needle at such a shallow depth, exemplary embodiments of the present invention provide at least one isolation feature to isolate the needle from forces.

In current steel cannula infusion sets which deliver to the subcutaneous layer, the needle is not isolated from any undesired forces which may cause pain when translated to the needle and the needle moves within the skin. Also, other intradermal devices face problems of premature or otherwise undesired needle removal when the device is bumped if the needle is not isolated from the forces.

In the exemplary embodiments of the present invention, the intradermal needle is isolated from outside forces by at least one feature. The fluid connector assembly is provided to shield the sensitive needle from direct contact with external forces. Proper inserter alignment is accomplished by providing a solid, fixed foundation for the user to release the ballistic inserter driving spring. Such a solid, fixed foundation is provided by the skin adhesive. The skin adhesive secures the set at a desired orientation, such that the ballistic inserter is also at a desired orientation of use. Accordingly, precise, repeatable insertions are accomplished via the adhesion.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. An infusion device that can insert an infusion needle at a controlled rate of speed to a depth to deliver medicament to the upper 3 mm of skin surface, comprising:

- an infusion device base, comprising at least one adhesive layer for releasably securing said infusion device base with said skin surface; and
- an inserter, wherein said inserter comprises an activation subassembly releasably secured to said infusion device base that is configured to release at least a user contact element and a driving spring from said infusion device base upon completed activation, and leave at least a needle with said infusion device base upon completed activation,
- wherein said user contact element comprises a turnkey, releasably coupled with said infusion device base and configured to release said driving spring of said inserter to insert said needle when turned relative to said skin surface, and further configured to release from said infusion device base when turned further relative to said skin surface.

2. An infusion device as claimed in claim 1, wherein said activation subassembly further comprises:

- a plunger, comprising said needle, wherein said plunger is configured to slidably enter and lock with said infusion device base when released by said turnkey and driven by said driving spring; and
- an activation collar, configured to couple with said turnkey and releasably couple with said infusion device base.

3. An infusion device as claimed in claim 2, wherein at least one of said turnkey, infusion device base and activation collar comprises a visual indicator for denoting at least one of a turnkey turning direction and a tube connection direction.

4. An infusion device as claimed in claim 1, further comprising an interface ring coupled with said infusion device base, wherein said ring is configured to extend from said infusion device base until said activation subassembly is released from said infusion device base after activation.

5. An infusion device as claimed in claim 1, further comprising a fluid connector assembly to releasably connect a tube to said base, wherein said fluid connector assembly comprises:

- a cover configured to cover said infusion device base via placement using a motion perpendicular to said skin surface; and
- a slide configured to secure said cover to said infusion device base via placement using a motion parallel to said skin surface, wherein said tube is connected to said slide, and wherein said slide comprises at least one cannula.

6. An infusion device as claimed in claim 1, wherein said driving spring of said inserter is configured to insert said needle at a speed greater than 3.3 ft/sec. (1.0 m/sec.).

7. An inserter that can insert an infusion needle at a controlled rate of speed to a depth to deliver medicament to the upper 3 mm of skin surface, comprising:

- an activation subassembly configured to be coupled with an infusion device base, comprising a user contact element, a driving spring, and a plunger, and configured to release at least said user contact element and said driving spring from said infusion device base upon completed activation, and leave at least said plunger with said infusion device base upon completed activation,
- wherein said user contact element comprises a turnkey, releasably coupled with said infusion device base and configured to release said driving spring of said inserter to insert said needle when turned relative to said skin surface, and further configured to release from said infusion device base when turned further relative to said skin surface.

8. An inserter as claimed in claim 7, wherein said activation subassembly further comprises:

- said plunger, comprising said needle, wherein said plunger is configured to slidably enter and lock with said infusion device base when released by said turnkey and driven by said driving spring; and an activation collar, configured to couple with said turnkey and releasably couple with said infusion device base.

9. An inserter as claimed in claim 8, wherein at least one of said turnkey, infusion device base and activation collar comprises a visual indicator for denoting at least one of a turnkey turning direction and a tube connection direction.

10. An inserter as claimed in claim 7, wherein said driving spring of said inserter is configured to insert said needle at a speed greater than 3.3 ft/sec. (1.0 m/sec.).

11. An infusion device base for receiving a partially integrated inserter that can insert a needle at a controlled rate of speed to a depth to deliver medicament to the upper 3 mm of skin surface, comprising:

at least one adhesive layer disposed upon a bottom skin contact surface of said infusion device base for securing said infusion device base to an infusion site;

at least one snap for releasably securing an activation subassembly of a partially integrated inserter to said infusion device base;

at least one snap for securing a plunger of said activation subassembly of said partially integrated inserter when driven into said infusion device base by a driving spring of said activation subassembly of said partially integrated inserter; and an interface ring moveably coupled with said infusion device base, wherein said ring is configured to contact said partially integrated inserter and in response extend from said bottom skin contact surface of said infusion device base and to contact said skin surface, and move substantially flush with said bottom skin contact surface of said infusion device base when said partially integrated inserter is removed.

12. An infusion device as claimed in claim 11, further comprising a fluid connector assembly to releasably connect a tube to said infusion device base, wherein said fluid connector assembly comprises:

a cover configured to cover said infusion device base via placement using a motion perpendicular to said skin surface; and a slide configured to secure said cover to said infusion device base via placement using a motion parallel to said skin surface, wherein said tube is connected to said slide, and wherein said slide comprises at least one cannula.

13. An infusion device base for receiving a partially integrated inserter that can insert a needle at a controlled rate of speed to a depth to deliver medicament to the upper 3 mm of skin surface, comprising:

at least one adhesive layer disposed upon a bottom skin contact surface of said infusion device base for securing said infusion device base to an infusion site;

at least one snap disposed upon a top surface of said infusion device base for releasably securing a partially integrated inserter; and an interface ring moveably coupled with said base, wherein said ring is configured to contact said partially integrated inserter and in response extend from said bottom skin contact surface of said infusion device base and to contact said skin surface, and move substantially flush with said bottom skin contact surface of said infusion device base when said partially integrated inserter is removed.

14. A method targeting a desired depth to deliver content to an upper skin surface, comprising the steps of:

placing an infusion device base upon an infusion site and activating a user contact element to release a driving spring to insert an infusion needle into said infusion site; and further activating said user contact element to release said user contact element and said spring from said infusion device base upon completed activation, and leaving at least said needle with said infusion device base upon completed activation.

15. A method as claimed in claim 14, further comprising the steps of:

connecting a cover of a fluid connector assembly to said infusion device base via placement using a motion perpendicular to a skin surface; and connecting a slide with said cover to secure said cover to said infusion device base via placement using a motion parallel to said skin surface, wherein said tube is connected to said slide.

16. A method as claimed in claim 14, further comprising the steps of:

turning a turnkey, releasably coupled with said infusion device base and configured to release said driving spring to insert said needle when turned relative to said skin surface, and further configured to release from said infusion device base when turned further relative to said skin surface.

17. A method as claimed in claim 14, further comprising the steps of:

pushing a pushable handle, releasably coupled with said infusion device base and configured to release said driving spring to insert said needle when pushed toward said skin surface, and further configured to release from said infusion device base when pushed further toward said skin surface.

* * * * *